United States Patent [19]

DiFulvio et al.

[11] 4,298,571
[45] Nov. 3, 1981

[54] INCUBATOR INCLUDING COVER MEANS FOR AN ANALYSIS SLIDE

[75] Inventors: Anthony P. DiFulvio; Michael R. Smith, both of Rochester, N.Y.

[73] Assignee: Eastman Kodak Company, Rochester, N.Y.

[21] Appl. No.: 159,550

[22] Filed: Jun. 16, 1980

Related U.S. Application Data

[63] Continuation of Ser. No. 751,872, Dec. 17, 1976, Pat. No. 4,224,032, and a continuation of Ser. No. 751,911, Dec. 17, 1976, Pat. No. 4,219,529.

[51] Int. Cl.³ .............................................. G01N 35/04
[52] U.S. Cl. ....................................... 422/65; 119/35; 422/64; 422/104
[58] Field of Search .......................... 23/230 R, 230 B; 422/64–66, 104; 424/3; 353/113; 119/35, 39, 43; 435/809

[56] References Cited

U.S. PATENT DOCUMENTS

3,728,227  4/1973  Elson et al. .
4,219,529  8/1980  Tersteeg et al. ..................... 422/65
4,224,032  9/1980  Glover et al. ........................ 422/65

Primary Examiner—Ronald Serwin
Attorney, Agent, or Firm—Donald D. Schaper

[57] ABSTRACT

An incubator is provided for use with a chemical analyzer of the type in which sample fluids are metered onto analysis slides which are subjected to analyses. The incubator includes a temperature-controlled chamber having a rotor mounted therein which supports slides in a plurality of slide-carrying positions. The slide-carrying positions of the rotor are individually indexable to transfer locations wherein slides may be placed on the rotor or removed therefrom. Cover means supported by the rotor include a plurality of covers associated with the slide-carrying positions. The covers are positionable to an operative position to partially enclose a sample fluid to control evaporation. Control means are provided to selectively move a cover from the operative position to permit an analysis slide to be positioned in the transfer location of the incubator or to be removed therefrom, without disturbing the sample fluid on the slide.

5 Claims, 7 Drawing Figures

INCUBATOR INCLUDING COVER MEANS FOR AN ANALYSIS SLIDE

This application is a continuation of Ser. No. 751,872, Dec. 17, 1976, now U.S. Pat. No. 4,224,032 and a continuation of Ser. No. 751,911, Dec. 17, 1976, now U.S. Pat. No. 4,219,529.

CROSS-REFERENCE TO RELATED APPLICATIONS

Reference is made to commonly-assigned, co-pending U.S. Patent Applications: Ser. No. 751,872, entitled METHOD AND APPARATUS FOR CHEMICAL ANALYSIS, filed in the names of Clyde P. Glover et al, on Dec. 17, 1976, and now U.S. Pat. No. 4,224,032 and a continuation of Ser. No. 751,911, entitled INCUBATOR FOR CHEMICAL ANALYZER, filed in the names of Glenn E. Tersteeg et al on Dec. 17, 1976, and now U.S. Pat. No. 4,219,529; Ser. No. 159,562, entitled APPARATUS FOR PROCESSING AN ANALYSIS SLIDE, filed in the names of Michael R. Smith et al, on even date herewith; and Ser. No. 159,564, entitled SLIDE DISTRIBUTOR FOR A CHEMICAL ANALYZER, filed in the names of Montalto et al on even date herewith.

BACKGROUND OF THE INVENTION

1. Field of the Invention

The invention relates to chemical apparatus for the automatic analysis of biological fluids, and more particularly, to cover means for cooperating with analysis slides in an incubator of such apparatus to control evaporation of sample fluids carried by the slides.

2. State of the Prior Art

In recent years, a number of automated systems have been developed for carrying out quantitative chemical analyses of sample fluids. In the aforementioned U.S. patent application Ser. No. 855,124, there is described a chemical analyzer in which a sample fluid is metered onto an analysis slide which is then transferred into an incubator. The incubator comprises a temperature-controlled chamber having a plurality of transfer locations wherein slides may be transferred into or out of the chamber; conveyor means rotatable in the chamber about a horizontal axis and having a plurality of slide-holding means for releasably holding the slides; and drive means for effecting movement of slides in the conveyor means within the chamber for positioning the slides for transfer at one of the transfer locations. This incubator, however, is not suitable for slides having fluids remaining in liquid form on a surface of the slide, since the slides are rotated through a vertical position in which the fluid would be spilled from the slide. The slide-holding means comprises a spring which cooperates with the slides to retain the slides in position on the conveyor.

U.S. Pat. No. 3,574,064, to Binnings et al, discloses apparatus in which glass slides are fed from a single supply station onto a turntable. Slides carried on the turntable are moved past a metering station, and then through wash and incubation stations spaced around the periphery of the turntable. Slides processed by the apparatus are ejected from the turntable into a slide receiver adjacent the slide supply station. There is no provision for automatic analysis of the processed slides, and they must be manually removed from the slide receiver for examination under a laboratory microscope. Further, there is no suggestion of a cover means for protection of the fluids on the slides.

An incubator, for use with analysis slides which are horizontally disposed in vertically-spaced slots in the incubator, is disclosed in RESEARCH DISCLOSURE, Vol. 175, November, 1978, Publication No. 17,569, published by Industrial Opportunities Limited, Homewell, Havant Hampshire, P09 1EF, United Kingdom. There is no suggestion in this publication, however, of means for controlling evaporation of fluids on analysis slides.

SUMMARY OF THE INVENTION

It is an object of the invention to provide novel and improved apparatus for controlling evaporation of fluids on analysis slides in an incubator of a chemical analyzer. The invention is particularly suitable for use in an analyzer adapted to perform analyses of biological fluids dispensed onto a generally planar test element, or analysis slide, of the type which is used to potentiometrically designate the activity of ions in the fluid. In such slides, a reference fluid and a sample fluid are metered onto the slide, and a measurement is taken of the potential developed in the slide.

In accordance with one aspect of the invention, the incubator comprises a temperature-controlled chamber for receiving and conditioning analysis slides. Conveyor means within the chamber is adapted to support the slides during the conditioning thereof and to deliver the slides to a transfer location in the chamber. Cover means in the chamber cooperates with analysis slides on the conveyor, and in an operative position, the cover means at least partially encloses fluids on the slides. Drive means effects movement of the conveyor to position slides at the transfer location. A control means is operable at the transfer location to move the cover means out of the operative position to permit transfer of the slides, without disturbing fluid carried on the slide.

In a preferred embodiment of the invention, the conveyor is in the form of a rotor having a plurality of slide-carrying positions. The cover means comprises a plurality of movable covers, and a movable cover is associated with each of the positions on the rotor. The control means comprises a lift mechanism at the transfer location which is adapted to lift a cover to permit a slide transfer mechanism to move a slide from the rotor to a read station.

DESCRIPTION OF THE PREFERRED EMBODIMENT

The invention is described hereinafter in connection with an analyzer for performing quantitative chemical analyses of biological fluids, such as blood serum. However, the invention is not so limited, and it can also be employed in other types of apparatus in which objects carrying fluids must be transferred from station to station and the fluids are subject to evaporation.

In accordance with a presently preferred embodiment of the invention, cover means are provided for cooperating with an analysis slide to control evaporation of a sample fluid from the slide. The cover means described and claimed is particularly suited for a chemical analyzer briefly disclosed herein and more fully described in the aforementioned U.S. Patent Application, entitled SLIDE DISTRIBUTOR FOR A CHEMICAL ANALYZER. Control of evaporation of the sample fluids is important with such an analyzer in that it is essential that concentrations of various constituents in the sample fluids not change, once the fluids have been metered onto a slide.

The invention is useful with analyzers in which the substrate which makes the testing of fluids possible comprises a pair of electrodes selective to the ion activity of choice. Recent developments have provided the electrodes in essentially planar, dry form suitable for use in pairs in an analyzer. An example of such a test element is disclosed in the patent to Hamblen et al, U.S. Pat. No. 4,053,381, granted on Oct. 11, 1977. This patent describes a test element, or analysis slide, of the type which is used to potentiometrically designate the activity of ions in a liquid test solution, and the disclosure of this patent is incorporated herein by reference.

The invention can also be used with other forms of test elements, as for example, the element disclosed in the commonly-owned patent to Przybylowitz et al, U.S. Pat. No. 3,992,158, granted on Nov. 16, 1976. The test element disclosed in this patent is formed as a multilayered element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular component present in the fluid.

Figure 1:
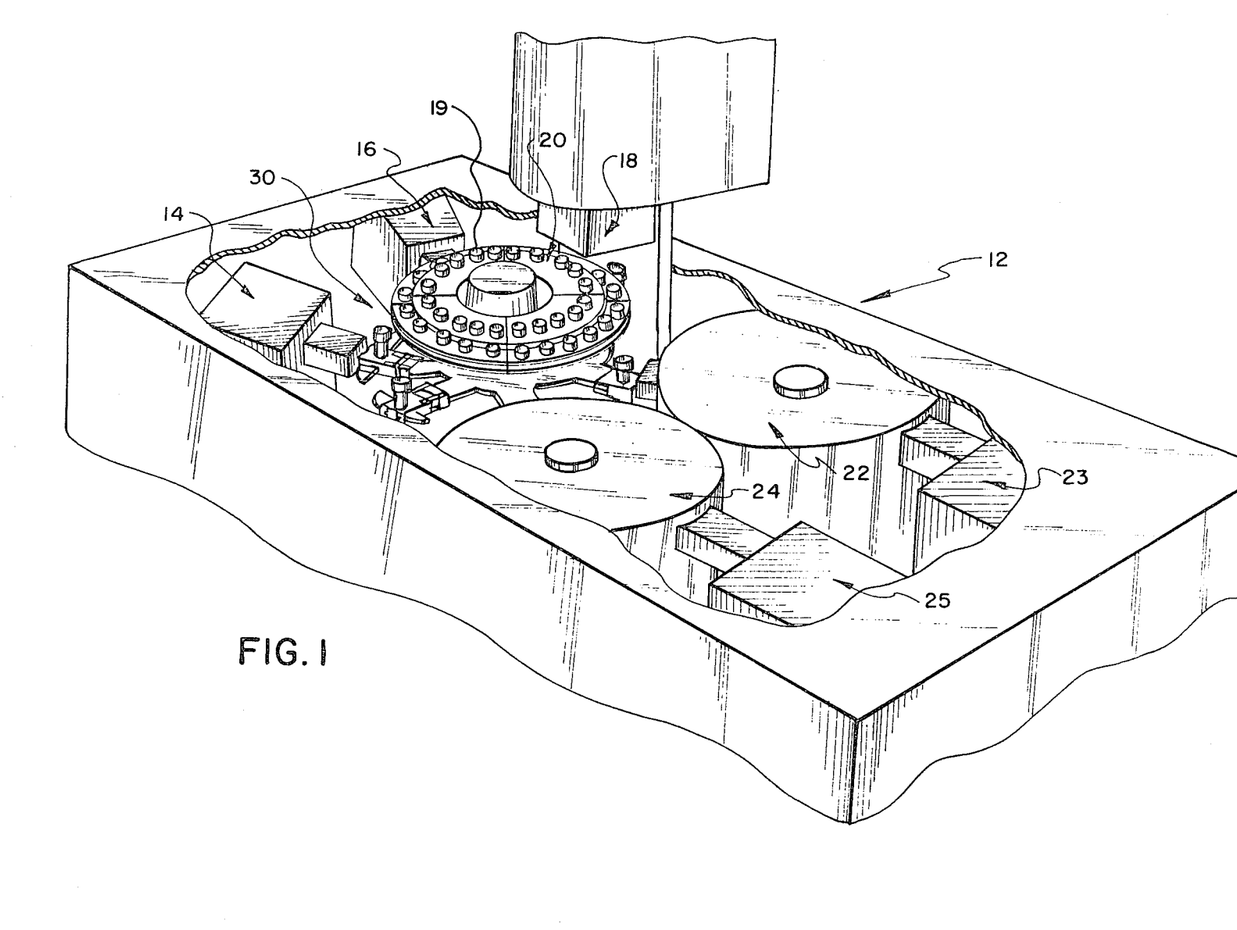
FIG. 1 is a perspective view of a chemical analyzer of the type which employs an incubator and cover means of the subject invention.

With reference to FIG. 1, there is shown analyzer apparatus 12 which comprises a housing 14 for a supply of analysis slides of the colorimetric type and a housing 16 for a supply of analysis slides of the potentiometric type. A metering device 18 is adapted to meter sample fluid from one of a plurality of cups 19 in a sample tray 20 onto an analysis slide in slide distributor 30. A second metering device, not shown, works in conjunction with metering device 18 to also deposit reference fluid onto the analysis slides of the potentiometer type. After the metering operations, analysis slides of the potentiometric type are deposited in an incubator 22 from slide distributor 30, and analysis slides of the colorimetric type are deposited in an incubator 24. Incubators 22, 24 are adapted to cooperate respectively with read stations, or analysis means, 23, 25, for measuring a change in the analysis slides as a result of the fluid deposited thereon. Slide transfer means are provided for removing the slides from the incubators 22, 24 to the analysis means 23, 25.

Figure 2:
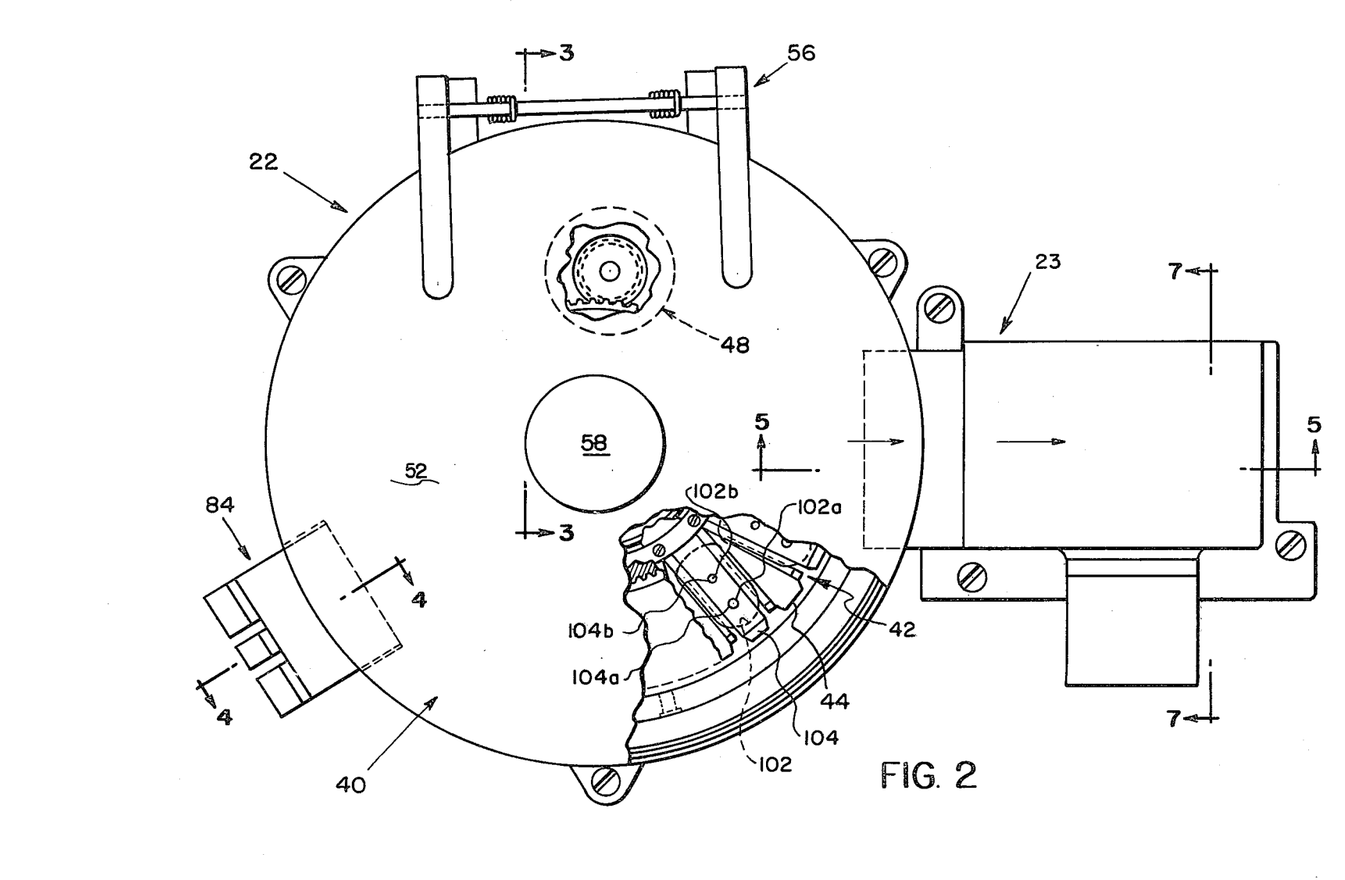
FIG. 2 is a top plan view of the potentiometric incubator and associated analyzer components, with portions broken away to show a preferred embodiment of the present invention.
Figure 3:
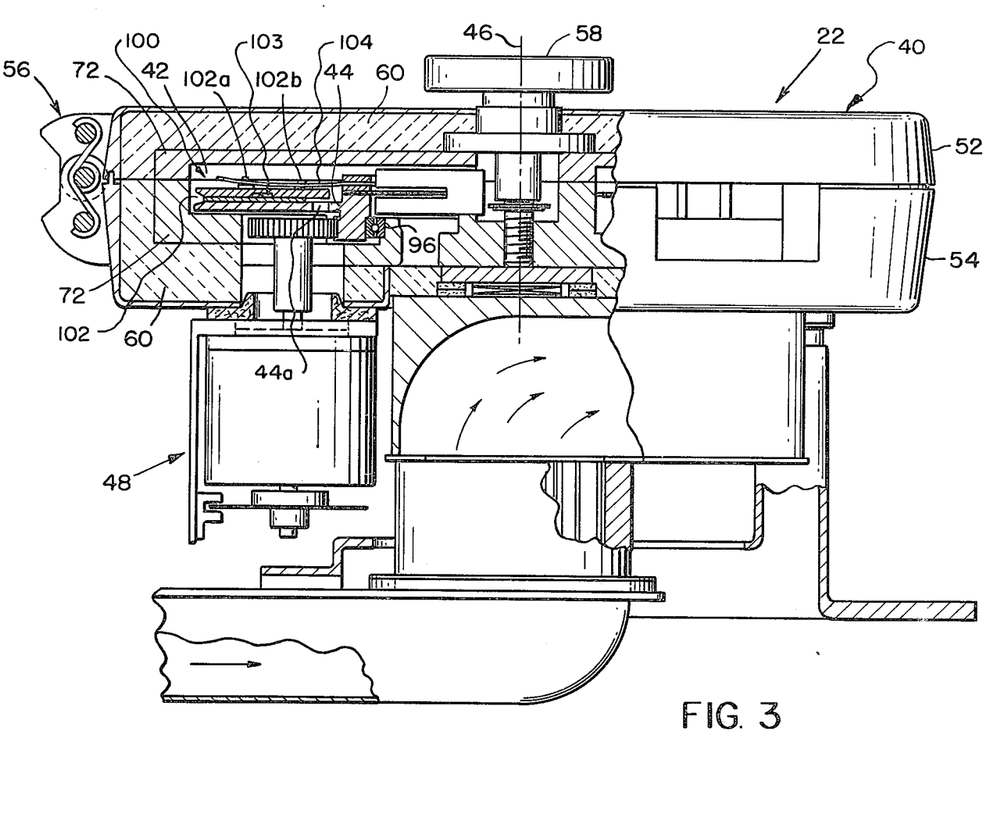
FIG. 3 is an elevational view of the potentiometric incubator, with a portion shown in section, taken along the line 3—3 in FIG. 2.

In FIGS. 2 and 3 there is shown incubator 22 comprising a housing 40 defining a generally cylindrical, temperature-controlled chamber 42, a circular slide conveyor or rotor 44 mounted for rotation within chamber 42 about a vertical axis designated 46, and a drive mechanism 48 for rotor 44. As will be described in greater detail, rotor 44 is suitable to receive slides 15 at an input position or transfer location 43, carry the slides in the chamber 42, and release the slides at an output position or transfer location 45. Housing 40 comprises, in part, a pair of mating sections 52, 54 which are joined by a hinge assembly 56. Section 52, through hinge assembly 56, may be pivoted from the closed position shown in FIG. 3, to an open or vertical position (not shown), permitting access to the chamber 42. In the closed position, section 52 is secured in place by a threaded fastener assembly 58 which screws into section 54. Each of the sections 52, 54 includes, at least in the area of the chamber 42, a double thickness of a suitable metal separated by a layer of insulation 60.

Temperature-control elements 72 are supported by sections 52, 54 proximate the outer portion of rotor 44. Preferably, the temperature-control elements 72 are in physical contact with each other, at least along the periphery, to permit heat transfer between the elements. This permits relatively accurate monitoring of the temperature of elements 72 by means of a single thermistor (not shown) supported in direct contact with one of the elements. The thermistor is connected to a control circuit, not shown, which includes a conventional feedback arrangement to maintain chamber 42 at a constant temperature, preferably 25° C. Other thermistors (not shown) may be positioned in the chamber proximate the rotor 44. Such an arrangement permits determination and calibration of temperature variations in the chamber 42.

Figure 4:
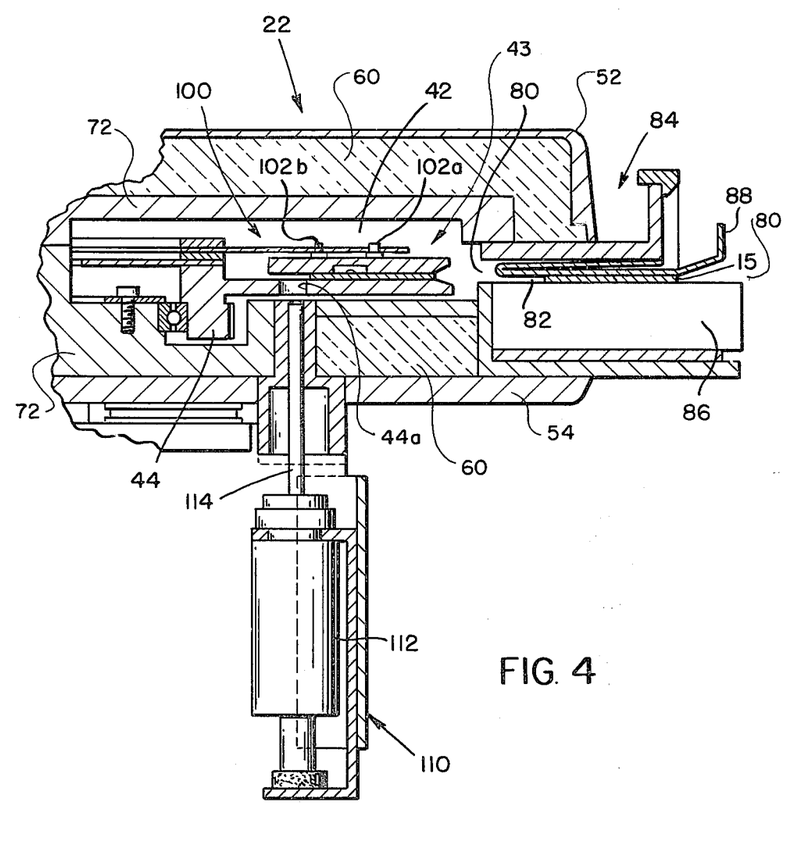
FIG. 4 is a sectional view of the delay station and a portion of the incubator, taken along the line 4—4 in FIG. 2.

With reference to FIG. 4, a slot 80 is of a shape and size sufficient to allow the passage of a slide 15 from the slide distributor 30 by a shuttle or transfer mechanism, not shown, into the delay station 84 where the slide 15 may be warmed or cooled to a desired temperature. Delay station 84 is supported relative to housing 40 such that an exit opening 82 communicates with load slot 80 to permit the slide 15 to be moved from the delay station 84 into the transfer location 43 of incubator 30. Delay station 84 comprises a support block 86 and a spring retainer 88 which is resiliently biased toward block 86. The spring retainer 88 holds slide 15 in position through contact with the edges of the slide until a shuttle mechanism moves the slide from the delay station 84 into the incubator.

Delay station 84 is adapted to bring the temperature of a slide 15 from ambient temperature to a temperature near the temperature maintained in the incubator chamber 42. Thus, a slide entering the transfer location 43 of chamber 42 does not materially affect the temperature therein, and a very precise temperature control can be maintained in the chamber. The support block 86 in delay station 84 is in physical contact with one of the temperature-controlled elements 72 and heat transfer between the block 86 and the heating element 72 provides for any desired alteration of the temperature of slide 15.

As shown in FIG. 3, rotor 44 is mounted for rotation within chamber 42 of housing 40. Rotor 44 is adapted to support a plurality of slides 15 at individual slide-carrying positions or stations for movement in a path about axis 46. Preferably, a plurality of openings 44a are defined in rotor 44 with each of the openings 44a being in a predefined location with respect to each of the slide-carrying positions. The purpose of these openings 44a will be explained hereinafter in greater detail. Rotor 44 is fixedly mounted in incubator 22 by a ring bearing 96. In the preferred embodiment, the rotor holds up to 17 slides and each is associated with slide cover means 100 carried by rotor 44. Rotor 44 may be driven by a drive mechanism 48 to advance rotor 44 in precise increments to position the slide-supporting stations in the transfer locations 43, 45 in the chamber 42 and to hold the rotor in position during loading and unloading operations. Drive mechanism 48 may include a stepper motor and function in a manner similar to that described in the aforementioned U.S. application Ser. No. 159,562.

Figure 5:
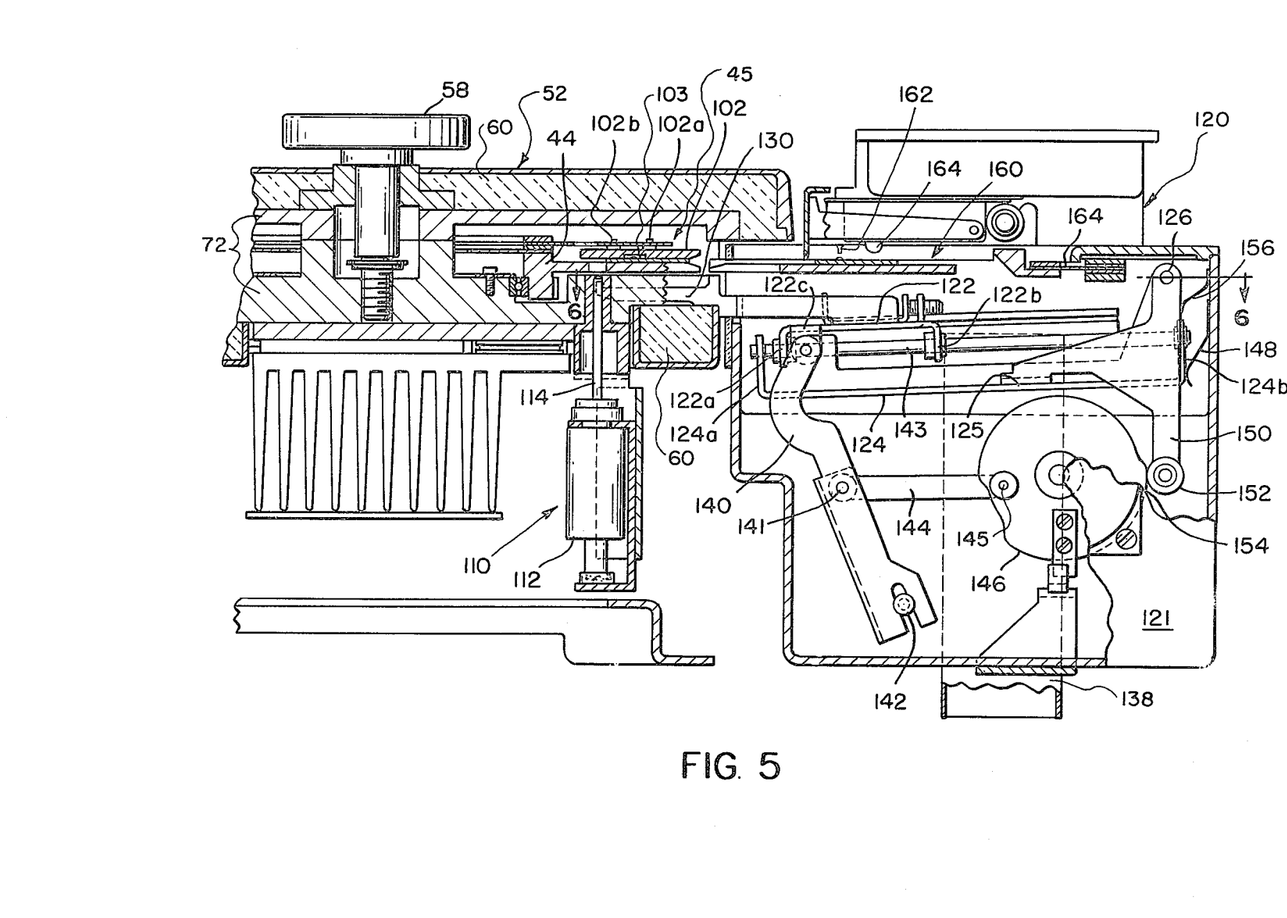
FIG. 5 is a sectional view of a portion of the incubator and analysis means, taken along the line 5—5 in FIG. 2.

With reference to FIGS. 3, 4, and 5, each of the slide cover means 100 comprises a cover 102 which is biased by a spring 104 to a covering position wherein the cover 102 is at rest against the slide 15. As will be appreciated, cover 102 cooperates with the slide 15 to at least partially enclose the fluid sample on the slide 15 and control evaporation of the fluid sample. The concentration of the sample fluid is thereby maintained approximately at the level which existed at the time of the metering of the fluid sample onto slide 15.

The covers 102 include a recess 103, which is aligned with the sample fluid on a slide 15 to receive in recess 103 any of the fluid sample which protrudes beyond the surface of slide 15. In this manner, the sample fluids are not disturbed by the covers 102. Covers 102 are of a non-porous material to eliminate gas absorption from the fluid samples on the slides and minimize the carry-over of reaction gases from slide to slide. Preferably, springs 104 define at least two apertures 104a, 104b, which mate with protruding extensions 102a, 102b of the evaporation covers 102 to align the covers and permit ready removal for periodic cleaning.

Lift mechanisms 110 are provided to lift covers 102 by a distance such that analysis slides 15 can be positioned on or removed from rotor 44 without disturbing fluids carried on the slides. Lift mechanisms 110 comprise a solenoid 112 which actuates a push rod 114 to pass through an opening 44a in the rotor 44 into engagement with a cover 102 to lift cover 102 at an appropriate time when the rotor 44 has been positioned with slide-carrying stations in the transfer locations 43, 45. The timing of the solenoid or any other motive device provided for lifting the covers 102 may be controlled by appropriate circuitry or fluidic control devices (not shown), to ensure that the solenoid is actuated only when the rotor has properly positioned a slide-carrying position in the transfer locations 43, 45.

Figure 6:
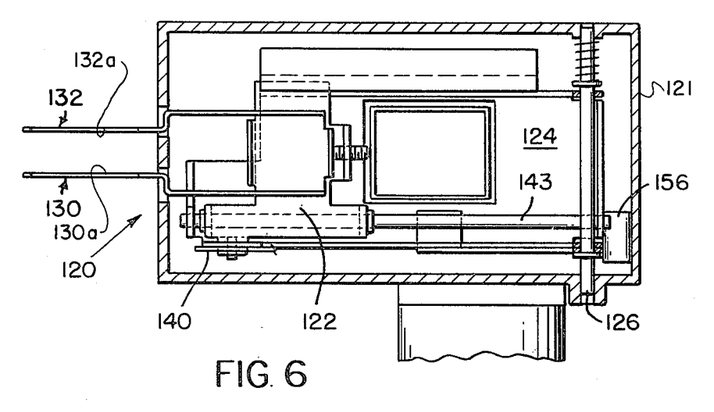
FIG. 6 is a sectional view of a slide transfer mechanism of the analyzer, taken along the line 6—6 in FIG. 5.
Figure 7:
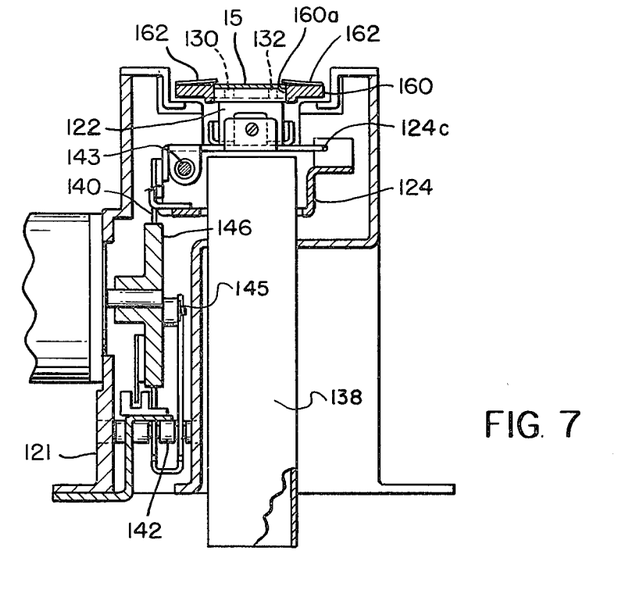
FIG. 7 is a sectional view of the slide transfer mechanism and analysis means, taken along the line 7—7 in FIG. 2.

A slide transporting mechanism 120, best shown in FIGS. 5, 6, and 7, is contained in a housing 121 and comprises a carriage 122 which is slidably mounted on a frame 124 pivotally supported at 126. Carriage 122 comprises fingers 130, 132, which are adapted to simultaneously move a first test slide from a sensing position in electrometer 60 to a waste receptacle 138 and a second slide from incubator 22 into the reading station. Fingers 130, 132 each includes a concave portion 130a, 132a, which is of suitable dimensions to receive a slide 15 therein when fingers 130, 132 are driven into receiving position in the chamber 42 of incubator 22.

Carriage 122 is supported by frame 124 and is reciprocally driven with respect thereto. In the preferred embodiment shown, a support guide or rod 143 affixed to tabs 124a, 124b of frame 124 passes through bushing supported in openings defined in a pair of tabs 122a, 122b extending from a first side of carriage 122. A second side of carriage 122 is captured and supported for movement in a direction parallel to the axis of rod 143 by a slide guide or groove 124c defined in frame 124.

Carriage 122 is reciprocally driven along a travel path defined by rod 143 and groove 124c by means of a crank arm 140 which is pivotally fastened by a pin to a tab 122c of carriage 122 and pivotally and slidably mounted at 142 to housing 121. Crank arm 140 is connected through a link 144 to a rotatably driven cam 146. A first end of link 144 is pivotally pinned to crank arm 140 at 141 and the second end of link 144 is coupled to cam 146 by a pin 145. Pin 145, through link 144, reciprocally drives carriage 122 to control movement of slides by the fingers 130, 132. A cam follower arm 150, also pivotally mounted at 126, comprises a roller 152 which rides on a peripheral cam surface 154 of cam 146. The cam follower arm 150 is biased in a clockwise direction, as shown in FIG. 5, and held in contact with cam surface 154 by a spring 156.

Frame 124 and carriage 122 are biased in a clockwise direction, as shown in FIG. 5, by a spring 148, and pivotal movement of frame 124 and carriage 122 is controlled by cam follower arm 150 which contacts frame 124 at 125. When roller 152 on follower arm 150 moves into a low portion of surface 154, follower arm 150 will rotate clockwise, permitting carriage 122 and frame 124 to also rotate in a clockwise direction. As carriage 122 rotates in a clockwise direction, it will move into contact with a platen 160.

As shown in FIG. 7, restraining members 162 are affixed to platen 160 and are adapted to cooperate with a slide 15 positioned in a channel 160a defined in plate 160. Platen 160 is supported for pivotal movement by means of flexure member 164 affixed to housing 121. Pivotal movement of carriage 122 will cause platen 160 to also be pivoted in a clockwise direction to move slide 15 supported on platen 160 into engagement with the pair of probes 162.

After contact of the slide 15 with the probes, further pivotal movement of the platen 160 will bring platen 160 into contact with semi-circular stops 164 of electrometer 60. At this point, pivotal movement of carriage 122 stops, but cam follower arm 150 may continue to rotate clockwise as roller 152 follows cam surface 154. During the continued rotation, cam follower 150 will break contact with frame 124 at 125. Such an over-drive feature ensures that the rotation of cam follower 150 is greater than that required to drive the platen 160 into contact with stops 164.

By always driving the platen 160 into stops 164, repeatable contact is made by probes 162 with each slide. After measurement of the potential developed in the slide, cam 146 is rotated to return the elements of picker mechanism 120 to the positions shown in FIG. 5.

In operation, slides 15 are sequentially loaded into incubator 22 after a predetermined time in delay station 84. Analyzer 12 is adapted to be continuously operated and the temperature within incubator 22 is controlled such that slides are ready to be analyzed in an analysis means 23 such as the type described more fully in the aforementioned U.S. Patent Application entitled APPARATUS FOR PROCESSING AN ANALYSIS SLIDE, after they have been moved by rotor 44 to the transfer location 45 in incubator 22. Following analysis, the slide 15 is removed from analysis means 23 and discarded.

A control system for incubator 22, as well as for other functions of analyzer 12, could include a computer, not shown, which may take any of the various forms known in the art that include programmable minicomputers and programmable microprocessors. The instructions and method of programming such computers is well known in the art, and thus, no further explanation is considered necessary. In the use of such a computer, input data including sample identification, calibration values, and desired tests for each sample would be keyed into the computer. Output signals from the computer would be utilized to provide input signals to the analyzer components to control their operation at the appropriate time in the machine cycle. Results from analysis means 23 would be transmitted to the computer which would perform the necessary calculations, according to a stored program, to arrive at a concentration for a particular sample. This information, along with sample identification would then be transmitted to a display or printout device.

The invention as been described in detail with particular reference to certain preferred embodiments thereof, but it will be understood that variations and modifications can be effected within the spirit and scope of the invention.

What is claimed is:

1. Apparatus for use in the analysis of fluids deposited on analysis slides, said apparatus comprising:
 means defining a temperature-controlled chamber for receiving and conditioning the analysis slides, said chamber having a transfer location at which slides can be transferred from said chamber;
 conveyor means in said chamber for supporting the slides during the conditioning thereof and for transporting a selected slide to said transfer location;
 cover means in said chamber for controlling evaporation of fluid on the slides, said cover means being positionable into an operative position to at least partially enclose slides on said conveyor and said cover means being positionable to a second position spaced from said operative position to permit said selected slide to be transferred at said location; and
 control means for positioning said cover means.

2. An incubator for a chemical analyzer of the type wherein a fluid metered onto an analysis slide is analyzed after an appropriate period of incubation, said incubator comprising:
 means defining a temperature-controlled chamber and openings in said chamber through which an analysis slide can be placed into or removed from said chamber;
 conveyor means having a plurality of slide-carrying positions for receiving analysis slides, said conveyor means being movably supported in said chamber to successively place said slide-carrying positions adjacent said openings;
 cover means for controlling evaporation of fluids on slides in said chamber, said cover means being movable to an operative position to at least partially enclose analysis slides on said conveyor means and to a second position spaced from said operative position to permit an analysis slide to be transferred into or out of one of said slide-carrying positions; and
 control means for selectively moving said cover means.

3. An incubator as set forth in claim 2 wherein said cover means comprises a plurality of covers, each of said covers being associated with a slide-carrying position for at least partially enclosing a slide received therein when said cover means is in the operative position.

4. An incubator as set forth in claim 3 wherein said control means comprises means supported by said incubator proximate said openings for selectively moving a cover associated with a slide-carrying position adjacent an opening.

5. Apparatus for analyzing a characteristic of fluids deposited on analysis slides, said apparatus comprising:
 means defining a temperature-controlled chamber for receiving and conditioning the analysis slides, said chamber having a transfer location at which slides can be transferred from said chamber;
 conveyor means having a plurality of slide-carrying positions for receiving analysis slides, said conveyor means being movably supported in said chamber to position said slide-carrying positions at said transfer location;
 a plurality of covers supported by said conveyor means with each of said covers being associated with a slide-carrying position and being movable, with respect to said conveyor means, between (1) a first position wherein said cover at least partially encloses a slide in a slide-carrying position to control evaporation of the fluid on the slide and (2) a second position wherein said cover is spaced from a slide in the slide-carrying position by a distance sufficient to permit said slide to be moved relative to said cover without disturbing the fluid on the slide; and
 means at said transfer location for selectively moving one of said covers from said first position to said second position.

* * * * *